United States Patent
Ottersbach et al.

(10) Patent No.: US 6,248,811 B1
(45) Date of Patent: Jun. 19, 2001

(54) BIOACTIVE SURFACE COATING

(75) Inventors: Peter Ottersbach, Windeck; Britta Mensing, Herne, both of (DE); Gerard Helary, Santeuil (FR); Marcel Jozefowicz, Lamorlaye (FR); Veronique Migonney, Eaubonne (FR); Jean-Pierre Vairon, Bourg la Reine (FR)

(73) Assignee: Huels Aktiengesellschaft, Marl (DE)

( * ) Notice: Subject to any disclaimer, the term of this patent is extended or adjusted under 35 U.S.C. 154(b) by 0 days.

(21) Appl. No.: 09/003,033

(22) Filed: Jan. 5, 1998

(30) Foreign Application Priority Data

| Jan. 3, 1997 | (DE) | 197 00 081 |
| Jan. 3, 1997 | (DE) | 197 00 082 |
| Jan. 3, 1997 | (DE) | 197 00 083 |
| Jul. 29, 1997 | (DE) | 197 32 588 |

(51) Int. Cl.$^7$ .................................................. C08K 5/09
(52) U.S. Cl. .................... 523/423; 522/149; 523/407; 524/68; 525/63; 525/71
(58) Field of Search ............................. 522/149; 523/407, 523/423; 524/68; 525/63, 71

(56) References Cited

U.S. PATENT DOCUMENTS

| 5,674,346 | * | 10/1997 | Kundel | 156/272.2 |
| 5,755,758 | * | 5/1998 | Woloszko | 607/116 |
| 5,788,687 | * | 8/1998 | Batich | 604/89.01 |
| 5,804,263 | * | 9/1998 | Goldberg | 428/34.7 |
| 5,811,151 | * | 9/1998 | Hendriks | 427/2.24 |
| 5,844,032 | * | 12/1998 | Serrano | 524/445 |
| 5,855,623 | * | 1/1999 | English | 8/115.96 |
| 5,858,514 | * | 1/1999 | Bowers | 428/195 |
| 5,869,127 | * | 2/1999 | Zhong | 427/2.12 |
| 5,885,566 | * | 3/1999 | Goldberg | 424/78.18 |

FOREIGN PATENT DOCUMENTS

| 0 431 213 | 6/1991 | (EP). |
| WO 92/18098 | 10/1992 | (WO). |
| WO 94/16648 | 8/1994 | (WO). |

OTHER PUBLICATIONS

Ranby, ACS Symp. Ser. 364, 168–186, 1988.*
Wang, J. Adhes. Sci. Technol 11, 1211, 1997.*
Noh, J. Polym. Sci., Part A 35, 3467–82, 1997.*
Ranby, Polym. Adv. Technol. 5, 829–36, 1994.*
Ruckert, Eur. Polym. J. 31, 431–435, 1995.*
Kubota, J. Appl. Polym. Sci. 48, 1717, 1993.*
Kubota, J. Appl. Polym. Sci. 41 689, 1990.*
S. Gorman, et al., Eur. J. Clin. Microbiol. Infect. Dis., vol. 12, No. 1, pp. 9–17, Jan. 1993, "Influence Of Selective Decontamination Of The Digestive Tract On Microbial Biofilm Formation On Endotracheal Tubes From Artificially Ventilated Patients".
Akihiko Kanazawa, et al., Journal Of Polymer Science: Part A: Polymer chemistry, vol. 31, PP. 1467–1472, 1993, "Polymeric Phosphonium Salts As A Novel Class Of Cationic Biocides. III. Immobilization Of Phosphonium Salts By Surface Photografting And Antibacterial Activity Of The Surface–Treated Polymer Films".
W. Kohnen, et al., ZBL. Bakt. Suppl. 26, pp. 408–410, 1994, "Staphylococcal Adherence To Modified Synthetic Polymer Surfaces".
B. Lassen, et al., Clinical Materials, vol. 11, pp. 99–103, 1992, "Some Model Surfaces Made By RF Plasma Aimed For The Study Of Biocompatibility".
Tatsuro Ouchi, et al., Prog. Polym. Sci., vol. 20, pp. 211–257, 1995, "Macromolecualr Prodrugs".
S.E. Tebbs, et al., Journal of Antimicrobial Chemotherapy, vol. 31, pp. 261–271, 1993, "A Novel Antimicrobial Central Venous Catheter Impregnated With Benzalkonium Chloride".
H. Yasuda, Journal of Polymer Science: Macromolecular Reviews, vol. 16, pp. 199–250, 252–293, 1981, "Glow Discharge Polmerization".

* cited by examiner

Primary Examiner—Christopher S. F. Low
Assistant Examiner—David Lukton
(74) Attorney, Agent, or Firm—Oblon, Spivak, McClelland, Maier & Neustadt, P.C.

(57) ABSTRACT

A process is disclosed for preparing bioactive, covalently fixed coatings on the surfaces of substrates, by grafting to a surface of the substrate a coating polymer which contains the following monomers in copolymerized form:

(i) at least one monomer of the general formula:

$$R\text{—}(A)_a \qquad (I),$$

in which
  R is a mono- or diolefinically unsaturated organic radical having a valence a,
  A is a carboxyl group, a sulfuric acid group, a sulfonic acid group, a phosphoric acid group, a phosphonic acid group, a phosphorous acid group, a phenolic hydroxyl group, or a salt of one of these acid groups, and
  a is 1, 2 or 3; and
(ii) at least one monomer which is sensitive to UV radiation.

16 Claims, 4 Drawing Sheets

BIOACTIVE SURFACE COATING

BACKGROUND OF THE INVENTION

1. Field of the Invention

The present invention relates to a process for coating surfaces, preferably polymer substrates, with coating polymers, which owing to the presence of specific functional groups, are fixed bioactively and covalently, i.e., permanently, on the surfaces. The coatings are anti-bacterial and can, moreover, be formulated so as to inhibit or promote cell proliferation thereon. The invention also relates to articles having surfaces coated in this way for, inter alia, medical or biotechnical purposes.

2. Description of the Background

The colonization and multiplication of bacteria on surfaces is a phenomenon which is in general unwanted and is frequently associated with disadvantageous consequences. For instance, in the drinking water and beverage industry bacterial populations may lead to health hazards. Bacteria on or in packaging frequently cause food contamination, or even infections in the consumer. In biotechnical plants that are to be operated under sterile conditions, bacteria alien to the system constitute a considerable processing risk. Such bacteria may be introduced with raw materials or may remain in all parts of the plant if sterilization is inadequate. By means of adhesion, sections of the bacterial population may escape the normal liquid exchange entailed in rinsing and cleaning and can multiply within the system.

Bacterial colonies are also known in water treatment plants (for example for membrane desalination) or else in containers which are filled with dissolved or liquid undiluted organic substances and which have advantageous conditions for bacterial populations. Such microbial colonization can, to a considerable extent, lead to the blocking and/or corrosive destruction of the plant.

Particular importance is attached to protecting against bacterial adhesion and propagation in nutrition, in human care, especially in the care of the elderly, and in medicine. In the case of large-scale outlets serving food or drinks there are considerable risks especially when, rather than using disposable tableware with its attendant problem of waste, reusable tableware is employed that is not adequately cleaned. Also known is the harmful propagation of bacteria in hoses and pipes which conduct foods, as is their multiplication in storage containers and in textiles in a hot and damp environment, for example in swimming baths. Facilities of this kind are preferred habitats for bacteria, as are certain surfaces in areas through which many people pass, for example in public transport vehicles, hospitals, telephone boxes and schools and, especially, in public toilets.

In the care of the sick and elderly, the often reduced defenses of the those affected necessitate careful measures to counter infections, especially in intensive care wards and in the case of care at home.

Particular care is required in the use of medical articles and instruments in the case of medical investigations, treatments and interventions, especially when such instruments or articles come into contact with living tissue or with body fluids. In the case of long-term or permanent contact, especially in the case of implants, catheters, stents, cardiac valves and pacemakers, bacterial contamination can become a life-threatening risk to the patient.

Diverse attempts have already been made to suppress the colonization and propagation of bacteria on surfaces. In J. Microbiol. Chemoth. 31 (1993), 261–271 S. E. Tebbs and T. S. J. Elliot describe paint-like coatings with quaternary ammonium salts as antimicrobial components. It is known that these salts are dissolved out of the coating material by water, by aqueous or other polar media and by body fluids, and that their action is therefore short-lived. This applies equally to the incorporation of silver salts in coatings, as described in WO 92/18098.

T. Ouchi and Y. Ohya in Progr. Polym. Sci. 20 (1995), 211 ff., describe the immobilization of bactericidal active substances on polymer surfaces by means of covalent bonding or ionic interaction. In such cases, the microbicidal actions are frequently reduced markedly relative to the pure active substance. Heteropolar bonds often prove to be of insufficient stability. Furthermore, the killing of the microbes leads in general to unwanted deposits on the surfaces, which mask the subsequent bactericidal action and form the basis for a subsequent bacterial colonization.

W. Kohnen et al. in ZB1. Bakt. Suppl. 26, Gustav Fischer Verlag, Stuttgart-Jena-New York, 1994, pages 408 to 410, report that the adhesion of *Streptococcus epidermidis* on a polyurethane film is reduced if the film is pretreated by glow discharge in the presence of oxygen and is then grafted with acrylic acid.

In many medical applications it is not only important that the surfaces be kept free from bacteria; rather, colonization with cells also has a part to play. In modern medicine frequent use is made of exogenous articles in such a way that they come into medium- or long-term contact with tissue or body fluids. Examples are implants, such as pacemakers, stents and prostheses, and also suture materials, drainage hoses and catheters. Such articles may consist, inter alia, of metals, ceramic and/or polymers. These materials must be biocompatible, i.e., compatible with the tissue and/or with the tissue fluids with which they are in contact. Numerous processes have been disclosed which are intended to make polymers biocompatible or to improve their biocompatibility. One of these methods is the colonization of the polymer surfaces with human cells.

On the other hand, there are medical applications where colonization of the surface of such exogenous articles with human cells is extremely undesirable. For instance, cell colonization in the case of catheters applied intracorporally in the medium term (indwelling catheters) is just as harmful as in the case of cardiac valves or stents which are implanted for the long term. WO 94/16648 describes a process by means of which it is intended to prevent the adhesion and proliferation of cells on the surface of implanted eye lenses made from polymer material. According to EP 0 431 213, polymers are equipped with cell-repelling properties by rendering their surface hydrophilic using strong mineral acids. This leads to a reduction in the cell adhesion.

The subsequent chemical modification of polymer surfaces, however, is usually not uniform. In many cases there remain areas which have not been treated, or not sufficiently treated, which form starting points for cell colonization. Furthermore, the cell-repelling properties of the treated surfaces are in many cases not persistent.

SUMMARY OF THE INVENTION

It is an object of the present invention to provide an improved process for the bioactive coating of surfaces by means of which surfaces can be kept substantially and persistently free from bacteria, for example cocci, in a physiologically compatible manner without thereby altering the mechanical properties of the treated materials or giving rise to any other of the disadvantages of the methods described above.

It is another object of the present invention to provide a process by means of which the antibacterial coatings may be formulated to additionally either inhibit or promote cell proliferation.

It has surprisingly been found that antibacterial, covalently fixed coatings may be prepared advantageously on the surface of substrates, especially polymer substrates, by grafting to a surface of a substrate a coating polymer which comprises, in copolymerized form, (i) at least one monomer of the general formula (I):

$$R\text{—}(A)_a$$

in which R is a mono- or diolefinically unsaturated organic radical having the valence a, A is a carboxyl group (—COOH), sulfuric acid group (—OSO$_2$OH), sulfonic acid group (—SO$_3$H), phosphoric acid group (—OPO(OH)$_2$), phosphonic acid group (—PO(OH)$_2$), phosphorous acid group (—OP(OH)$_2$), a phenolic hydroxyl group, or a salt of one of these groups, and a is 1, 2 or 3; and (ii) at least one monomer which is sensitive to UV radiation.

A more complete appreciation of the invention and many of the attendant advantages thereof will be readily obtained as the same becomes better understood by reference to the following detailed description when considered in connection with the accompanying drawings.

DETAILED DESCRIPTION OF THE INVENTION

Figure 1:
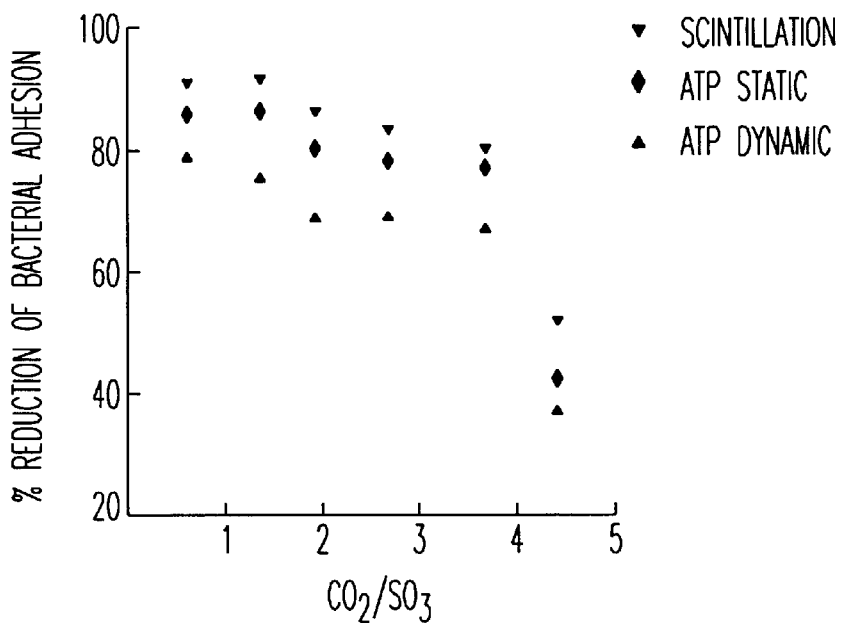
FIG. 1. Reduction in adhesion of *Staphylococcus aureus* on films coated in accordance with the invention, as a function of the molar COO$^-$/SO$_3^-$ ratio FIG. 2. Reduction in adhesion of *Staphylococcus epidermidis* on films coated in accordance with the invention, as a function of the molar COO$^-$/SO$_3^-$ ratio FIG. 3. Reduction in adhesion of *Staphylococcus pyogenes* on films coated in accordance with the invention, as a function of the molar COO$^-$/SO$_3^-$ ratio FIG. 4. Reduction in adhesion of *Klebsielia pneumoniae* on films coated in accordance with the invention, as a function of the molar COO$^-$/SO$_3^-$ ratio FIG. 5. Reduction in adhesion of *Pseudomonas aeruginosa* on films coated in accordance with the invention, as a function of the molar COO$^-$/SO$_3^-$ ratio FIG. 6. Reduction in adhesion of *Escherichia coli* on films coated in accordance with the invention, as a function of the molar COO$^-$/SO$_3^-$ ratio FIG. 7. Reduction in cell growth of human fibroblasts on coated films, as a function of the molar COO$^-$/SO$_3^-$ ratio
Figure 2:
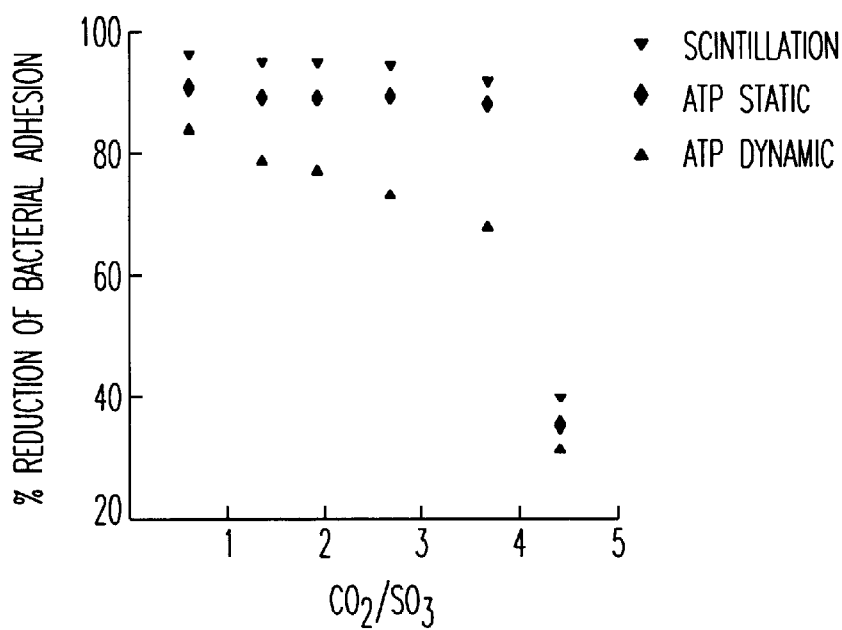
Figure 3:
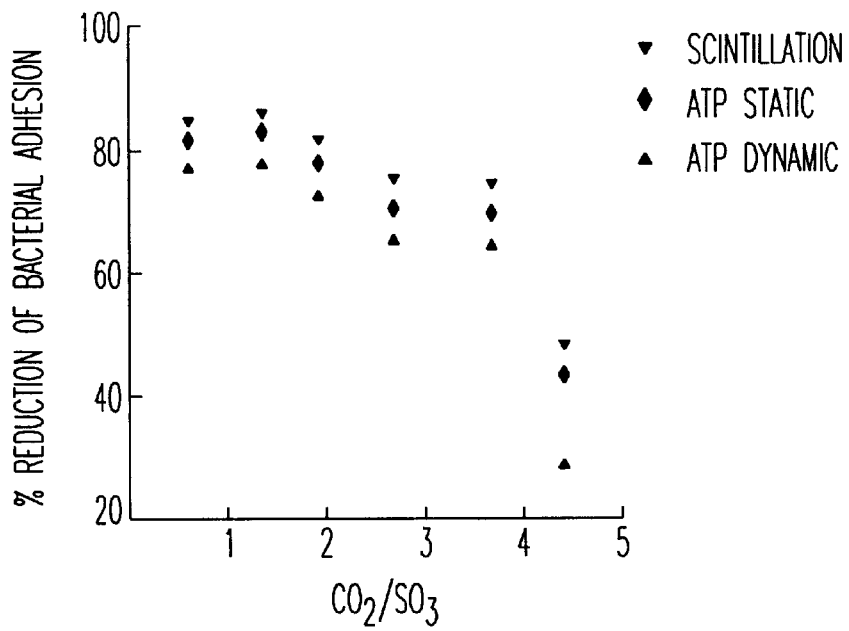
Figure 4:
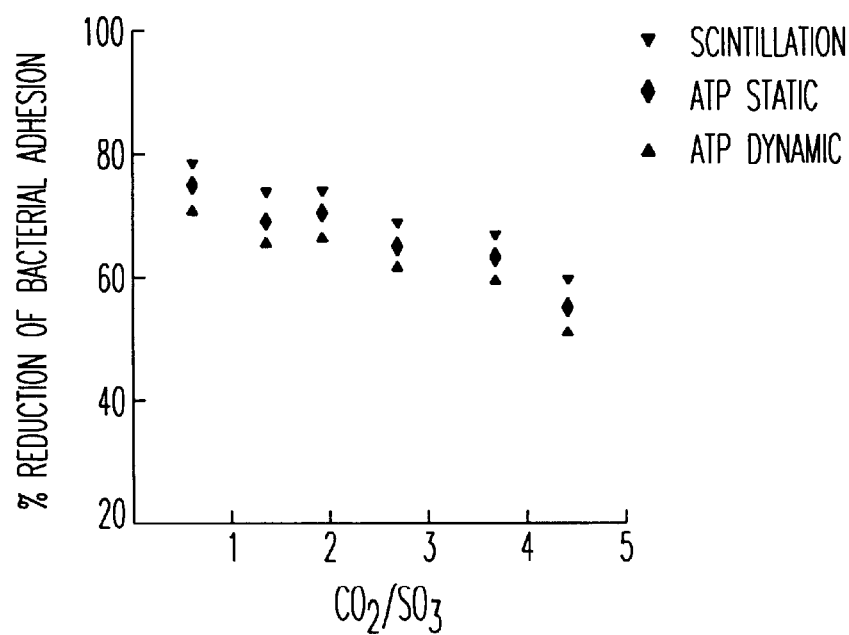
Figure 5:
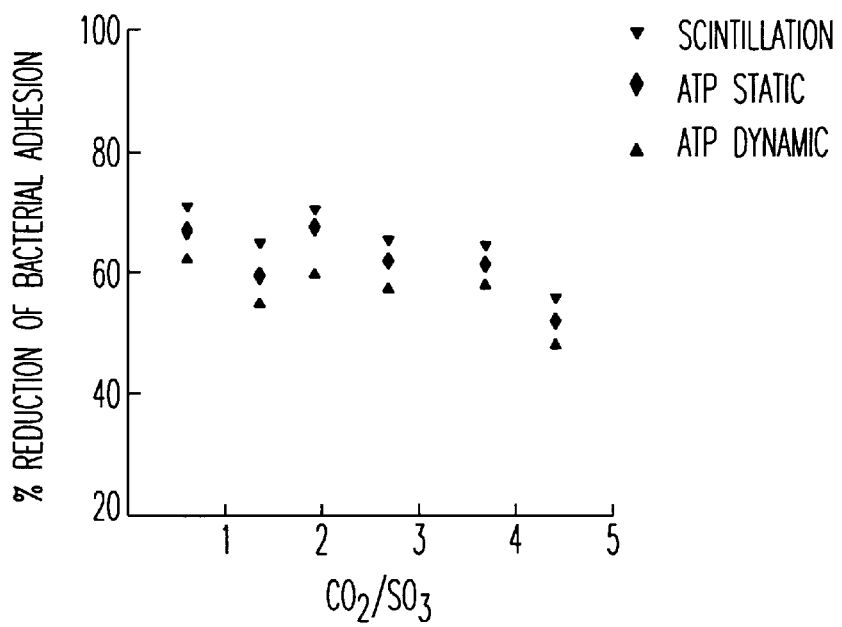
Figure 6:
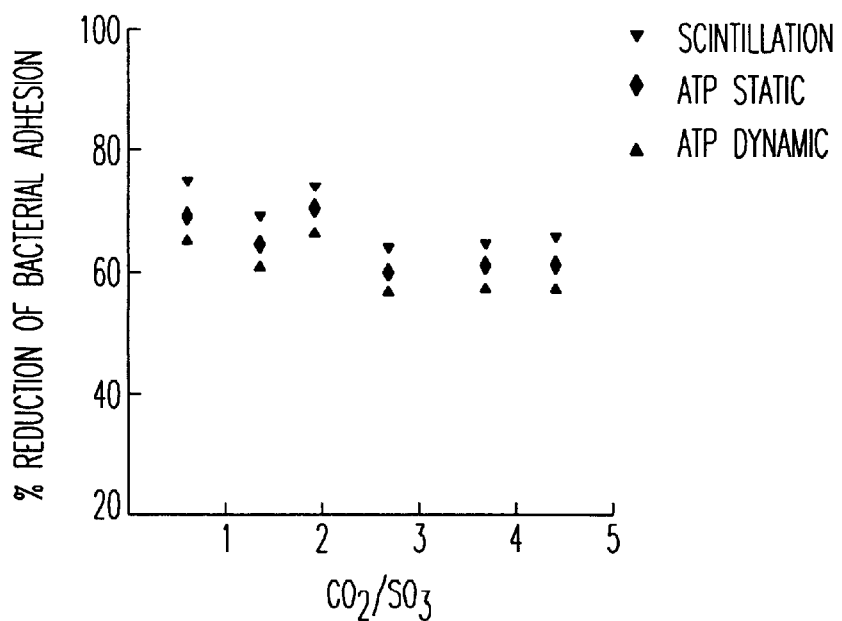

The organic radical R may have a hydrocarbon structure, or may comprise additional atoms in addition to carbon and hydrogen, for example oxygen, nitrogen and/or silicon atoms. R may be a radical of a phenolic compound. Preferably, R has 2 to 20 carbon atoms, more preferably 2 to 10 carbon atoms.

When the coating polymer comprises a monomer I having a carboxyl group or a salt of the carboxyl group (i.e., a carboxylate group) then, preferably, either this monomer has at least one further radical A which is not a carboxyl group or a carboxylate group, or the coating polymer having at least one additional monomer I in which A is not a carboxyl group or a carboxylate group. In this way, the relatively weak antibacterial action of the carboxyl group or a salt thereof may be intensified.

Among the salts of groups specified for A, preference is given to the alkali metal salts and, in particular, to sodium salts. A common feature of the monomers of the formula I is that they have 1 or 2 olefinic double bonds and also at least one acidic group or a salt of an acidic group.

Coatings produced on various substrates by plasma-induced graft polymerization are known, for example, from B. Lassen et al., Clinical Materials 11 (1992), pages 99–103, and have been investigated for biocompatibility. In that case, however, only monomers sensitive to UV radiation were grafted, and no mention is made of grafting onto activated substrate surfaces. Moreover, plasma is not an optimal polymerization initiator. H. Yasuda refers accordingly, in J. Polym. Sci.: Macromolecular Review, Vol. 16 (1981), 199–293, to the undefined and uncontrollable chemistry of plasma polymerization. This may be acceptable for some purposes, but is problematic for medical and biotechnical applications, for the precise reason that a special criterion here is reproducible coatings of consistently high quality.

The surfaces modified in accordance with the invention may reduce the adhesion of bacteria to a high extent even over a prolonged period. The bacterial strains whose adhesion is reduced or prevented in accordance with the invention include, for example, *Staphylococcus aureus, Staphylococcus epidermidis, Streptococcus pyogenes, Klebsiella pneumoniae, Pseudomonas aeruginosa, Escherichia coli,* and *Enterobacter faecium*. The coated surfaces are free from migratable and/or extractable monomer and oligomer components. Unwanted side effects resulting from released exogenous substances or from dead bacteria may be avoided from the outset. The surfaces of the grafted-on coatings are therefore of outstanding physiological compatibility. The particular conditions under which the surfaces, in addition to their properties of bacterial inhibition, have a cell proliferation-inhibiting or -promoting effect will be discussed below.

In the process according to the invention the optionally activated substrate surfaces are first coated with the coating polymers, and the coating may then be fixed covalently, i.e., permanently, to the substrate surface by gentle grafting of the ready-formed coating polymer under the action of UV radiation.

1. The Coating Polymers

The coating polymers have at least one copolymerized monomer of the general formula I whose functional group A is responsible for the bioactive (i.e., antibacterial) properties of the polymeric coating. These monomers I include monomers of the general formulae II and III:

| $(C_nH_{2n-q-x})(COOR^1)_x$ | Formula II |
| $(C_nH_{2n-q-x})(SO_3R^1)_x$ | Formula III | which are preferred monomers for the preparation of the coating polymers. Coating polymers which contain not only at least one monomer II but also at least one monomer III have a particularly strong antibacterial action, it being possible for the radicals $(C_nH_{2n-q-x})$ to be identical or different. In the formulae II and III:

n independently at each occurrence is an integer from 2 up to and including 6;

x independently at each occurrence is 1 or 2;

q independently at each occurrence is 0 or 2, and the radical $R^1$, independently at each occurrence, is —H or an equivalent of a metal ion, advantageously an alkali metal ion and, in particular, a sodium ion.

In accordance with the definitions given, the radical $(C_nH_{2n-q-x})$ independently at each occurrence is a straight-chain or branched monovalent alkenyl radical (q=0, x=1) or alkadienyl radical (q=2, x=1) or a divalent alkenylene radical (q=0, x=2) or alkadienylene radical (q=2, x=2).

Instead of two monomers II and III it is also possible to employ only one monomer (II+III) which contains the $COOR^1$ and $SO_3R^1$ groups in the same molecule.

In addition, benzene-derived monomer components of the formula IV

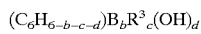   Formula IV are within the scope of formula I and can be present advantageously as monomers in the coating polymer, where B independently at each occurrence is a mono- or diolefinically unsaturated straight-chain or branched radical of the formula $(C_nH_{2n-1-q-x})(COOR^1)_x$ or $—(C_nH_{2n-1-q-x})(SO_3R^1)_x$, in which $R^1$, n, q and x are as defined above.

$R^3$ independently at each occurrence is $C_{1-4}$-alkyl, $—NH_2$, $—COOH$, $—SO_3H$, $—OSO_3H$, $—OPO(OH)_2$, $—PO(OH)_2$, $—OP(OH)_2$, $—PO(O^-)OCH_2CH_2N^+(CH_3)_3$, $—PO(O^-)OCH_2CH_2N^+(CH_3)_3$, $—OP(O—CH_2CH_2N^+(CH_3)_3$, or a salt thereof, preferably an alkali metal and, more preferably, a sodium salt;

b is 1, 2 or 3;

c is 0, 1, 2 or 3; and d is 0, 1, 2 or 3;

with the proviso that b+c+d is $\leq 6$, advantageously $\leq 4$.

Other suitable monomers for preparing the coating polymers which are grafted onto the activated substrate surface are, in accordance with the formula I, olefinically unsaturated, acidic sulfuric esters and their salts; sulfonic acids and their salts; phosphonic acids and their neutral or acidic salts; phosphoric esters and their neutral or acidic salts; and phosphorous esters and their neutral or acidic salts. Finally, mention may also be made of phenols having a functionality (or basicity) of from 1 to 3 and containing olefinic groups, and also their salts, corresponding to the formula I, as suitable monomers.

The coating polymers can, of course, in every case, and not only as in the above-mentioned case of the monomers II and III, contain different A radicals, which is achieved through an appropriate choice of monomers having different A radicals.

Of the monomers of the general formulae I to IV which are suitable for preparing the coating polymers and which comprise one or more identical or different radicals A in the molecule, mention may be made, by way of non-limiting example, of acrylic acid, methacrylic acid, 4-vinylsalicylic acid, itaconic acid, vinylacetic acid, cinnamic acid, 4-vinylbenzoic acid, 2-vinylbenzoic acid, sorbic acid, caffeic acid, maleic acid, methylmaleic acid, dimethylmaleic acid, dihydroxymaleic acid, isocrotonic acid, fumaric acid, methylfumaric acid, allylacetic acid and the alkali metal salts, especially the sodium salts, of these acids; vinylsulfonic acid, allylsulfonic acid, methallylsulfonic acid, 4-styrenesulfonic acid, 2-styrenesulfonic acid, vinyltoluenesulfonic acid, 4-carboxy styrenesulfonic acid and the alkali metal salts and especially the sodium salts of these sulfonic acids; diprimary 1,3-butadiene-1,4-diol diphosphate, 4- and 2-vinylphenol, 2-allylhydroquinone and 4-vinylresorcinol, and the corresponding salts.

In addition to the monomers of the general formulae I to IV it is also possible for other monomers to be present in the coating polymer which may make little or no contribution to the bioactive properties of the coating. Examples of these monomers include, for example, vinyl ethers, such as vinyl methyl ether and vinyl butyl ether; vinyl esters, such as vinyl acetate and vinyl propionate; vinyl ketones, such as vinyl ethyl ketone and vinyl n-butyl ketone; nitriles, such as acrylonitrile and methacrylonitrile; carboxamides, such as acrylamide, N,N-dimethylacrylamide and methacrylamide; carboxylic anhydrides, such as maleic anhydride; carboxylic esters, such as methyl acrylate, ethyl acrylate, 2-ethyl hexyl acrylate, methyl methacrylate, 2-hydroxy ethyl acrylate, 2-(2'-hydroxyethoxy)ethyl acrylate, 2-hydroxy-1-methyl ethyl acrylate, 2-N,N-dimethylamino ethyl acrylate, npropyl methacrylate, 2-hydroxy ethyl methacrylate, 2-(2'-hydroxyethoxy)ethyl methacrylate, 2-hydroxy-1-methyl ethyl methacrylate, 2-N,N-dimethylamino ethyl methacrylate, diethylene glycol methacrylate, triethylene glycol diacrylate, ethyl vinylsulfonate and 2-hydroxyethyl vinylsulfonate; olefins and diolefins, such as 1-butene, 1-hexene, 1-octene, 1,3-butadiene, isoprene and chloroprene; vinylsiloxanes and other silicon-containing vinyl monomers, such as tris(trimethylsiloxy)methacryloylpropylsilane and tris(trimethylsiloxy)acryloylpropylsilane. These or other monomers may even be present in the predominant amount, for example up to 90 mol-%. Accordingly, these other monomers may comprise 0 to 90% mol % of the total monomers used in the polymer. This range includes all specific values and subranges therebetween, including 5, 10, 25, 50, and 75 mol %.

Monomers having groups which can be converted into groups A may be regarded as potential monomers of the formula I. They include primarily esters, anhydrides, acid amides and nitrites which can be hydrolyzed at least on the surface—and it is only this which is important in terms of bioactive properties—in a known manner using acid or alkali to give carboxyl or carboxylate groups or sulfonic acid or sulfonate groups, respectively. For as long as this is not taking place, these monomers are regarded as additional, non-bioactive monomers within the meaning of the present invention.

Preferred coating polymers contain in copolymerized form (a) monomers with carboxylic acid and/or carboxylate groups and (b) monomers with sulfonic acid and/or sulfonate groups. The molar proportions of these monomers in the coating polymers together being generally from 5 to 40%, advantageously from 5 to 30% and, in particular, from 15 to 20%. These ranges include all specific values and subranges therebetween, including 10, 25, and 35 mol %.

The molar ratio of the monomers (a) to the monomers (b) is advantageously <10, especially <5. Pronounced antibacterial properties are shown by coating polymers in which this ratio is from 0.5 to 10, advantageously from 0.5 to 5. If the ratio is in the range from 0.4 to 3, advantageously from 0.4 to 2, the coating polymers show not only the antibacterial action but also strong cell proliferation-inhibiting properties. If the ratio is in the range from 2 to 10, advantageously from >3 to 5, the coating polymers, surprisingly, have cell proliferation-promoting properties. A coating inhibits cell proliferation, in the sense of the invention, when the adhesion and multiplication of mammalian cells on the coating is reduced relative to the uncoated substrate. The coating is regarded as being cell proliferation-promoting within the context of the invention if the adhesion and multiplication of mammalian cells on the coating is improved in comparison with the uncoated substrate, or is in any case less adversely affected than the adhesion of bacteria.

From the standpoint of compatibility there are three possible two-way combinations of the groups specified, namely carboxyl and sulfonic acid groups, carboxyl and sulfonate groups, and carboxylate and sulfonate groups, and also two possible three-way combinations, namely carboxyl, carboxylate and sulfonate groups, and carboxyl, sulfo acid and sulfonate groups. All of these combinations constitute advantageous coatings in the sense of the invention. It is of course also possible, as mentioned above, subsequently to convert groups which are present in the coating polymer into functional groups A, for example carboxamide groups (originating, for example, from acrylamide) into carboxyl groups by hydrolysis in an acidic medium. Furthermore, carboxyl groups and sulfonic acid groups can be converted by neutralization (for example in phosphate buffers)into carboxylate and sulfonate groups, respectively. In every case this alters the abovementioned molar ratio of the monomers (a) and (b), possibly with quantitative or even qualitative consequences for the properties of the coating polymer.

An important constituent of the coating polymers is (ii) a copolymerized monomer having a group which is sensitive to UV radiation. As used herein, the term "sensitive to UV radiation" means that the copolymerized monomer contains a functionality which is capable of reacting with the surface to be coated during the grafting reaction, in order to covalently attach the coating polymer to the surface. Suitable such monomers are all those which after copolymerization still have at least one reactive double bond which enables the coating polymer to be grafted onto the activated substrate surface. Examples which may be mentioned are vinylic cinnamoyl or furyl derivatives, and especially cinnamoylethyl acrylate or methacrylate. The monomer which is sensitive to UV radiation is advantageously employed in amounts from 1 to 20 mol-%, advantageously from 3 to 15 mol-%, based on the overall monomers. In the course of free-radically initiated polymerization, the double bond which is $\alpha$ to the benzene ring is retained as a group sensitive to UV radiation for the subsequent grafting.

The polymers may be prepared in conventional manner by free-radically initiated polymerization, advantageously by solution or emulsion polymerization. Examples of suitable solvents are water; ketones, such as acetone, methyl ethyl ketone and cyclohexanone-ethers, such as diethyl ether, tetrahydrofuran and dioxane; alcohols, such as methanol, ethanol, n- and isopropanol, n- and isobutanol and cyclohexanol, strongly polar solvents, such as dimethylformamide, dimethylacetamide and dimethyl sulfoxide; hydrocarbons, such as heptane, cyclohexane, benzene and toluene; halogenated hydrocarbons, such as dichloromethane and trichloromethane, esters, such as ethyl acetate, propyl acetate and amyl acetate; and also nitrites, such as acetonitrile.

Examples of suitable polymerization initiators are azo nitriles, alkyl peroxides, acyl peroxides, hydroperoxides, peroxy ketones, peroxy esters and percarbonates, and all customary photoinitiators. The polymerization may be initiated thermally, for example by heating at from 60 to 100° C., or by radiation having an appropriate wavelength. After the end of the exothermic polymerization reaction the polymer is separated off from the solvent in a customary manner, for example by precipitation with water, provided the solvent is soluble in water. Monomeric or oligomeric constituents may be removed by extraction with an appropriate solvent.

2. The Substrate Materials

The nature of the substrate to be coated may vary widely. At least a portion of at least one surface of the substrate is coated with the bioactive polymer coating of the present invention. Preferably, the entire surface is coated with the bioactive polymer. Particularly suitable substrate materials are all polymeric substrates, such as polyurethanes, polyamides, polyesters and polyethers, polyether-blockamides, polystyrene, polyvinyl chloride, polycarbonates, polyorganosiloxanes, polyolefins, polysulfones, polyisoprene, polychloroprene, polytetrafluoroethylene (PTFE), polysiloxanes, corresponding copolymers and blends, and also natural and synthetic rubbers, with or without radiation-sensitive groups. The process according to the invention can also be applied to surfaces of painted or otherwise polymer-coated metal, glass or wooden structures. The surfaces of the substrate materials are advantageously freed from adhering oils, greases and other contaminants in a known manner using a solvent before the coating with the coating polymers. They may, but need not necessarily, be activated before the coating, as described below. The activation is in some cases carried out in order to achieve better adhesion of the grafted coating to the substrate material. In general, however, the coatings on unactivated substrate surfaces are virtually no different from coatings on activated surfaces with respect to the biological effects and with respect to adhesion.

3. Activation of the Substrate Surfaces

The polymeric substrates may be activated, if desired, by the following methods.

3.1. In the case of the preparation of the substrate polymers it is possible to incorporate, by copolymerization, monomers having groups which are sensitive to UV radiation, in a similar way to that described for the coating polymers. Monomers suitable for this purpose are the same as those which may also be present in the coating polymers. These monomers can be employed, for example, in amounts from 1 to 20 mol-%, advantageously from 3 to 15 mol-%. Polymers modified in this way for sensitivity to radiation can be prepared in a customary manner by means of free-radically initiated polymerization in solution, emulsion or suspension.

3.2. Alternatively, the activation of standard polymers without UV-sensitive groups can be effected by UV radiation, for example in the wavelength range from 100 to 400 nm, preferably from 125 to 310 nm. A suitable source of radiation is, for example, a HERAEUS Noblelight UV excimer device, Hanau, Germany. Mercury vapor lamps, however, are also suitable for substrate activation provided they emit considerable fractions of radiation within the stated ranges. The exposure time is in general from 0.1 second to 20 minutes, preferably from 1 second to 10 minutes, depending on the wavelength and intensity of radiation. It has been found that the presence of oxygen is advantageous. The preferred oxygen pressures are between $2 \times 10^{-5}$ and $2 \times 10^{-2}$ bar. The operation is conducted, for example, in a vacuum of from $10^{-4}$ to $10^{-1}$ bar or using an inert gas, such as helium, nitrogen or argon, with an oxygen content of from 0.02 to 20 parts per thousand.

3.3. Activation can also be achieved in accordance with the invention by means of a high-frequency plasma or microwave plasma (Hexagon, Technics Plasma 85551 Kirchheim, Germany) in air or a nitrogen or argon atmosphere. The exposure times are in general from 30 seconds to 30 minutes, preferably from 2 to 10 minutes. The energy employed in the case of laboratory devices is between 100 and 500 W, preferably between 200 and 300 W.

3.4. It is also possible to use corona devices (SOFTAL, Hamburg, Germany) for activation. The exposure times in this case are in general from 1 second to 10 minutes, preferably from 1 to 60 seconds.

3.5. Activation by electron beams or gamma rays (for example from a cobalt 60 source) allows for shorter exposure times which are in general from 1 to 60 seconds.

3.6. Flame treatments of surfaces likewise lead to their activation. Suitable devices, especially those having a barrier flame front, can be constructed in a simple manner or obtained, for example, from ARCOTEC, 71297 Mönsheim, Germany. They can be operated with hydrocarbons or hydrogen as combustion gas. In every case, harmful overheating of the substrate must be avoided, which is easily achieved by means of intimate contact with a cooled metal surface on the substrate surface facing away from the side subjected to flame treatment. Activation by flame treatment is restricted, accordingly, to relatively thin, flat substrates, such as sheets. The exposure times amount in general to from 0.1 second to 1 minute, preferably from 0.5 to 2 seconds, the flames involved being—without exception—nonluminous and the distances of the substrate surfaces from the external flame front being from 0.2 to 5 cm, preferably from 0.5 to 2 cm.

3.7. Furthermore, the substrate surfaces can also be activated by treatment with strong acids or strong bases. Suitable strong acids which may be mentioned are sulfuric acid, nitric acid and hydrochloric acid. Polyamides, for example, can be treated at room temperature with concentrated sulfuric acid for from 5 seconds to 1 minute. Particularly suitable strong bases are alkali metal hydroxides in water or in an organic solvent. Thus, for example, dilute sodium hydroxide solution can be allowed to act on the substrate surface at from 20 to 80° C. for from 1 to 60 minutes. Alternatively, for example, polyamides can be activated by allowing 2% strength KOH in tetrahydrofuran to act on the surface for from 1 minute to 30 minutes.

3.8. In some cases, for example with highly hydrophobic polymers, it may be advisable to activate the substrate surfaces by a combination of two or more of the methods specified. Very generally, a proven method of substrate activation is that in which the incorporation of UV-sensitive groups (3.1) is combined with UV irradiation (3.2).

4. Coating by Graft Polymerization

After one of the activating pretreatments described under 3.2 to 3.8, the substrates with the activated surfaces may be exposed for from 1 to 20 minutes, preferably from 1 to 5 minutes, to the action of oxygen, for example in the form of air. Alternatively, a solvent, such as tetrahydrofuran, can be allowed to act on the activated surfaces for a similar length of time. Subsequently, the surfaces that have been activated (including those which have if desired been activated in accordance with 3.1), but also those which have not been activated, are coated by known methods, such as dipping, spraying or brushing, with a solution of the coating polymer which is to be used in accordance with the invention. Solvents which have been found suitable are, for example, ethers, such as tetrahydrofuran, and/or strongly polar solvents, such as dimethyl sulfoxide, although other solvents can also be used provided they have sufficient solvency for the monomers and provide good wetting of the substrate surfaces. Depending on the solubility of the polymers and on the desired film thickness of the grafted coating, the concentrations of the polymer in the solution can be in general from 0.1 to 50 percent by weight. Solutions with a content of coating polymer of from 3 to 15% by weight, advantageously of about 10% by weight, have been found appropriate in practice and give rise in general and in one pass to coherent coatings which cover the substrate surface and have film thicknesses which can be more than 0.1 $\mu$m.

Following or even during the evaporation of the solvent, the grafting of the applied coating polymer is brought about, judiciously by radiation in the short wave segment of the visible region or in the long wave segment of the UV region of electromagnetic radiation, to form covalent bonds to the substrate surface. Highly suitable radiation, for example, is that of a UV excimer of the wavelengths 250 to 500 nm, preferably from 290 to 320 nm. Here again, mercury vapor lamps have been found suitable provided they emit considerable fractions of radiation within the stated ranges. The exposure times are in general from 10 seconds to 30 minutes, preferably from 2 to 15 minutes.

In some cases it is judicious to repeat the above-described operations, optionally including the activation, in order by means of such a multicoat technique to ensure a hermetically sealed and/or relatively thick coating. Alternatively, it is also possible to immerse the optionally surface-activated substrate, if desired after the oxygen or solvent treatment described above, into the solution of the coating polymer which is to be used in accordance with the invention and to irradiate it in the immersed state. By means of simple experiments it is not difficult to ascertain the irradiation times with a given radiation source and the substrate/solution contact times, which may be relatively long, required to achieve the desired film thickness.

The process according to the invention for the antibacterial modification of the surface of substrates, and especially polymer substrates, permits the precise establishment of molar ratios of different functional groups which are optimal for inhibiting bacterial adhesion and/or propagation and for regulating cell proliferation behavior. It is a particular advantage of the process and of the coated substrates according to the invention that the latter, moreover, show good blood compatibility. Furthermore, the process offers the advantage that plastics which have already become established can, while retaining their mechanical properties and their form, be additionally modified so as to be antibacterial and, alternatively, to inhibit or to promote cell proliferation. No further treatments before or after are necessary as long as problem-free wetting and chemical bonding to the substrate surfaces are possible. Highly hydrophobic plastics may require a hydrophilicizing pretreatment, for example by chemical etching with acids or bases or by plasma treatment, in order to attain sufficient wettability by the solution of the coating polymer. In this case the highly hydrophobic plastics are hydrophilicized at the same time and surface-activated in the sense of the present invention.

Articles which have been coated in accordance with the processes of the present invention and thereby modified to make them antibacterial are suitable as biocompatible materials for use in the biotechnical and/or medical fields, for example for storage or packaging purposes or for hoses or pipelines. Examples of medical articles are catheters, hoses, wound drainage devices, dressings, stents, intraocular lenses, pacemakers and cardiac valves.

The substrates an articles may also used as implants in patients in need thereof. The substrates/articles of the present invention may be implanted into a patient in need thereof according to the well-known procedures routinely used in the field of biomedical implants. As used herein, the terms "implant" and "implanted" include articles and substrates that are applied to the skin surface of a patient, e.g., a wound dressing, as well to articles which are implanted into the body, e.g., pacemakers and cardiac valves. In these applications, the substrate and article implants are contacted with the biological fluid of the patient.

Having generally described this invention, a further understanding can be obtained by reference to certain specific examples which are provided herein for purposes of illustration only and are not intended to be limiting unless otherwise specified.

EXAMPLES

The coating polymers used in the examples are representative of a large number of other polymers having monomers which fall under the formulae I to IV.

(1) Investigations of Bacterial Adhesion

Measurement of the Bacterial Adhesion on Films of Coating Polymers by Scintillation These films were prepared in order to compare their antibacterial properties with those of antibacterially coated substrate films according to the invention.

Samples of the coating polymers (Examples 1 to 9 below) obtained by copolymerization are dissolved in an appropriate solvent, such as chloroform. The solutions are poured into a Petri dish and the solvent is evaporated, and then the resulting polymer films are immersed for a period of one hour in 1 ml of a solution consisting of 0.4 g/l bovine serum albumin (BSA), dissolved in phosphate-buffered physiological saline solution (PBS), and 20 µg/ml purified human fibronectin. The samples thus coated with fibronectin are then placed with vigorous stirring for 1 hour at 37° C. in a suspension of the respective bacteria, which have been radiolabeled by incorporation of $^3$H-thymidine. After the predetermined period has elapsed the excess bacteria are removed by washing, and the polymer films are rinsed twice with 3 ml each time of a PBS-BSA solution, and, in order to determine the number of adhering bacteria, are placed in a glass vessel with a screw closure containing 20 ml of scintillation solution. The percentage of adhering bacteria is determined by way of the ratio of the radioactivity present in the sample to the radioactivity introduced originally by the bacteria. The inhibition of bacterial adhesion is expressed as a percentage relative to the bacterial adhesion of an untreated film as an external standard.

Measuring the Bacterial Adhesion of Coated Standard Films by ATP Determination (Static)

Following adsorption of the bacterial cells on immersed polymer films, the nonadhering bacteria are rinsed off with sterile PBS buffer solution. Adenosine triphosphate (ATP), a substance present in the cells, is extracted from the adhering bacteria in a customary manner and is determined using a customary commercial test combination in a bioluminometric assay. The number of light pulses measured is proportional to the number of adhering bacteria. In each case, a number of film sections are employed. The value measured with the uncoated, standard film is taken as being equal to one hundred percent, and the bacterial adhesion values of the antibacterially coated films are expressed as a percentage reduction.

Measuring the Bacterial Adhesion of Coated Standard Films by ATP Determination (Dynamic)

The bacteria are placed together with the section of film to be tested in a yeast extract/peptone/glucose nutrient solution and are shaken at 37° C. for 24 hours. Following this, the section of film is rinsed with tapwater, transferred to a fresh flask containing nutrient solution, and shaken at 37° C. for a further 24 hours. This cycle is repeated once more, and the film section is rinsed with tapwater. The adenosine triphosphate (ATP), a substance present in cells, is extracted from the bacteria which are adhering to the film and is determined using a customary commercial test combination in a bioluminometric assay. Since the boundary conditions applying to the dynamic measurement are the same as those for the static measurement, the bacterial adhesion values of the coated films are expressed as a percentage reduction in comparison with uncoated, standard films.

(2) Investigations of Cell Proliferation

Conditioning the Polymer Films (Substrate Films)

The films coated in accordance with the invention, and uncoated comparison films, are washed twelve times for 3 hours each time at 37° C. in ethanol. The films pretreated in this way are subsequently washed three times for 3 hours in each case in a 0.15-molar sodium chloride solution and then rinsed off with water. In the following purification step, the films are placed three times for 3 hours in each case into a phosphate buffer solution and then irradiated with UV light for 15 minutes. The films thus pretreated are stored for 16 hours at 37° C. in a DMEM (Dulbecco's Modified Eagles Medium) solution. Finally, the films are kept for 16 hours at 37° C. in a DMEM solution to which 0.05% antibiotics, 200 mg/l L-glutamine and 10% fetal calf serum are added, under an atmosphere of 5% $CO_2$ and 95% air.

Preparing the Cell Suspension

Human fibroblasts (McCoy's) from ATCC No. CRL 1996 (Rockville, Md., USA) are grown in a DMEM medium containing 0.05% antibiotics, 200 mg/l L-glutamine and 10% fetal calf serum at 37° C. under an atmosphere of 5% $CO_2$ and 95% air. After isolating the cells from the nutrient medium, both the number of living cells and the total number of cells are determined in a customary manner.

Measuring the Cell Proliferation Properties

The films coated in accordance with the invention and the comparison films, following the pretreatment described above, are then placed in wells in standard microliter plates and held by means of special PTFE inserts which have been sterilized beforehand with ethanol. Films, wells and PTFE inserts are sterilized by irradiation with UV light for 16 minutes. Subsequently, the cell suspension is added to the polymer films. After incubation for 8 days at 37° C. the cells are purified by means of phosphate buffer solution, separated off with 0.05% by weight trypsin-EDTA solution, and counted optically or using a cell counter.

(3) Preparation of the Coating Polymers

Example 1

A monomer mixture comprising 5 mol %-tris (trimethylsiloxy)methacryloyloxypropylsilane (TTMPS), 10 mol % cinnamoylethyl methacrylate (CEM), 13.7 mol % methacrylic acid (MA) and 11.3 mol % dimethyloctylammonium styrenesulfonate (DOASS) is introduced into a reaction vessel in THF as solvent under inert gas, and this initial charge is heated to 65° C. On reaching this temperature, 0.6 mol % of azobisisobutyronitrile is added. After a reaction period of 24 hours, the quaterpolymer is isolated by removing the solvent on a rotary evaporator and then is washed with water. NMR analysis of the product reveals a composition of

| TTMPS | CEM | MA | DOASS | |
|-------|-----|------|-------|-------|
| 72 | 8.2 | 10.8 | 9 | mol % |

The ratio of COOH or COO$^-$ to $SO_3^-$ is 1.2.

Example 2

A monomer mixture comprising 75 mol % tris(trimethylsiloxy)methacryloyloxypropylsilane (TTMPS), 10 mol % cinnamoylethyl methacrylate (CEM), 10 mol % methacrylic acid (MA) and 5 mol % dimethyloctylammonium styrenesulfonate (DOASS) is introduced into a reaction vessel in THF as solvent under inert gas, and this initial charge is heated to 65° C. On reaching this temperature, 0.6 mol % of azobisisobutyronitrile is added. After a reaction period of 24 hours, the quaterpolymer is isolated by removing the solvent on a rotary evaporator and then washed with water. NMR analysis of the product reveals a composition of

| TTMPS | CEM | MA | DOASS | |
|---|---|---|---|---|
| 84 | 9.6 | 2.1 | 3.8 | mol % |

The ratio of COOH or COO⁻ to $SO_3^-$ is 0.55.

Example 3

55 mol % of methyl methacrylate, 35 mol % of methacrylic acid, 5 mol % of sodium styrenesulfonate and 5 mol % of cinnamoylethyl methacrylate are dissolved in dimethyl sulfoxide under inert gas. After reaching the reaction temperature of 70° C., 0.6 mol % of azobisisobutyronitrile, dissolved in dimethyl sulfoxide, is added dropwise. After a reaction period of 18 hours the product is precipitated with ice-water and subsequently subjected to extraction with acetone and water in a Soxhlet. Drying is conducted at 50° C. in vacuo.

Example 4

65 mol % of methyl methacrylate, 18 mol % of methacrylic acid, 12 mol % of sodium styrenesulfonate and 5 mol % of cinnamoylethyl methacrylate are dissolved in dimethyl sulfoxide under inert gas. After reaching the reaction temperature of 75° C., 0.6 mol % of azobisisobutyronitrile, dissolved in dimethyl sulfoxide, is added dropwise. After a reaction period of 16 hours the product is precipitated with ice-water and subsequently subjected to extraction with acetone and water in a Soxhlet. Drying is conducted at 50° C. in vacuo.

Example 5

80 mol % of methyl methacrylate, 10 mol % of acrylic acid, 5 mol % of sodium styrenesulfonate and 5 mol % of cinnamoylethyl methacrylate are initially introduced in dimethyl sulfoxide under inert gas. After reaching the reaction temperature of 75° C., 0.6 mol % of azobisisobutyronitrile, dissolved in dimethyl sulfoxide, is added dropwise. After a reaction period of 16 hours the product is precipitated with ice-water and subsequently subjected to extraction with acetone and water in a Soxhlet. Drying is conducted at 50° C. in vacuo.

Example 6

87.5 mol % of methyl methacrylate, 5 mol % of maleic anhydride, 2.5 mol % of sodium styrenesulfonate and 5 mol % of cinnamoylethyl methacrylate are initially introduced in dimethyl sulfoxide under inert gas. After reaching the reaction temperature of 70° C., 0.6 mol % of azobisisobutyronitrile, dissolved in dimethyl sulfoxide, is added dropwise. After a reaction period of 16 hours the product is precipitated with ice-water and subsequently subjected to extraction with acetone and water in a Soxhlet. Drying is conducted at 50° C. in vacuo.

Example 7

80 mol % of methyl methacrylate, 8 mol % of methacrylic acid, 7 mol % of sodium styrenesulfonate and 5 mol % of cinnamoylethyl methacrylate are initially introduced in dimethyl sulfoxide under inert gas. After reaching the reaction temperature of 70° C., 0.6 mol % of azobisisobutyronitrile, dissolved in dimethyl sulfoxide, is added dropwise. After a reaction period of 16 hours the product is precipitated with ice-water and subsequently subjected to extraction with acetone and water in a Soxhlet. Drying is conducted at 50° C. in vacuo.

Example 8

85 mol % of methyl methacrylate, 7.5 mol % of maleic anhydride, 2.5 mol % of sodium styrenesulfonate and 5 mol % of cinnamoylethyl methacrylate are initially introduced in dimethyl sulfoxide under inert gas. After reaching the reaction temperature of 70° C., 0.6 mol % of azobisisobutyronitrile, dissolved in dimethyl sulfoxide, is added dropwise. After a reaction period of 18 hours the product is precipitated with ice-water and subsequently subjected to extraction with acetone and water in a Soxhlet. Drying is conducted at 50° C. in vacuo.

Example 9

65 mol % of methyl methacrylate, 18 mol % of methacrylic acid, 12 mol % of triethylammonium styrenesulfonate and 5 mol % of cinnamoylethyl methacrylate are initially introduced in dimethyl sulfoxide under inert gas. After reaching the reaction temperature of 70° C., 0.6 mol % of azobisisobutyronitrile, dissolved in dimethyl sulfoxide, is added dropwise. After a reaction period of 16 hours the product is precipitated with ice-water and subsequently subjected to extraction with acetone and water in a Soxhlet. Drying is conducted at 50° C. in vacuo.

The radiation-sensitive monomer used, cinnamoylethyl methacrylate, is obtained starting from 2-hydroxyethyl methacrylate (3.8 mmol) and cinnamoyl chloride (3.8 mmol) in 100 ml of dry ethyl ether at room temperature in the presence of 3.8 mmol of pyridine.

Example 10

A monomer mixture comprising 59 mol % of tris (trimethylsiloxy)methacryloyloxypropylsilane (TTMPS), 16 mol % of cinnamoylethyl methacrylate (CEM), 13.7 mol % of methacrylic acid (MA) and 11.3 mol % of dimethyloctylammonium styrenesulfonate (DOASS) in THF as solvent is heated to 65° C. under nitrogen as protective gas. When this temperature is reached, 0.6 mol % of azobisisobutyronitrile (AIBN) in THF is metered in as solvent over a period of 1 hour. After a reaction time of 24 hours, the quaterpolymer is isolated by removing the solvent in a rotary evaporator and then washed with water. NMR analysis of the product provides a composition of

| TTMPS | CEM | MA | DOASS | |
|---|---|---|---|---|
| 66.7 | 13.1 | 11.6 | 8.6 | mol % |

The ratio of COOH or COO⁻ to $SO_3^-$ is 1.4.

Example 11

A monomer mixture comprising 60.4 mol % of tris (trimethylsiloxy)methacryloyloxypropylsilane (TTMPS), 18 mol % of cinnamoylethyl methacrylate (CEM), 9.5 mol % of methacrylic acid (MA) and 12.1 mol % of dimethyloctylammonium styrenesulfonate (DOASS) in THF as solvent is heated to 65° C. under nitrogen as protective gas. When this temperature is reached, 0.6 mol % of azobisisobutyronitrile (AIBM) in THF is metered in as solvent over a period of 1 hour. After a reaction time of 24 hours, the quaterpolymer is isolated by removing the solvent in a rotary evaporator and is then washed with water. NMR analysis of the product provides a composition of

| TTMPS | CEM | MA | DOASS | |
|-------|-----|-----|-------|---|
| 68.5 | 13.8 | 7.6 | 10.1 | mol % |

The ratio of $COOH/COO^-$ to $SO_3^-$ is 0.8.

(4) Grafting the Coating Polymers onto Substrate Films

The grafting is carried out using the cinnamoyl-containing grafting polymers prepared above. The substrates were coated by photografting. The coating polymers of Examples 1 to 9 were grafted onto activated polymeric substrates and the coating polymers of Examples 10 and 11 onto unactivated polymeric substrates.

The grafting of the coating polymers onto activated surfaces was carried out as follows:

The activation is carried out by UV irradiation using a Hg vapor lamp (100 M, and the grafting is initiated by irradiation with the same lamp.

The various substrate films are irradiated for 20 minutes and then immersed in THF for 15 minutes.

A solution of the coating polymer (10 g/l) in THF-dimethyl sulfoxide (80/20) is sprayed onto 2 samples of the substrate film.

The two samples are irradiated for 10 minutes.

The grafting onto unactivated surfaces was carried out as follows:

2 samples of a silicone (polysiloxane) substrate film are sprayed with a solution of the quaterpolymer (10 g/l) in THF/dimethyl sulfoxide (80:20).

The samples are irradiated for 10 minutes using a 100 W mercury vapor lamp (distance between sample and lamp 2 cm).

The grafting is demonstrated by the substrate having an increase in weight of 15.9% (Example 10) and 18.3% (Example 11) after extraction with water (6 h at 60° C.). Crosslinking and grafting occur by means of the double bonds in the α position:

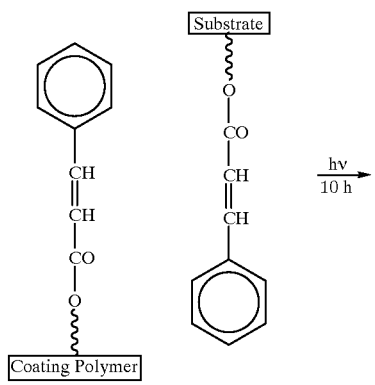

-continued

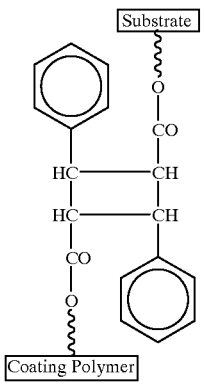

Photocrosslinking by means of the radiation-sensitive groups can be observed using IR spectroscopy. Whereas the IR spectrum of the substrate already coated with the coating polymer but not yet subjected to UV irradiation has a band at $1637\ cm^{-1}$, which is assigned to the C=C double bonds, following UV irradiation this band can no longer be detected.

(5) Results of the Test for Bioactive Properties

The results of the test for bioactive properties of the coated substrate films are evident from FIGS. 1–7. FIGS. 1 to 6 demonstrate the antibacterial properties of the coating polymers according to the invention. The scintillation values are obtained with films of the coating polymers. It is seen that the antibacterial properties of the substrate films coated in accordance with the invention are very similar to those of the films of the coating polymers.

Figure 7:
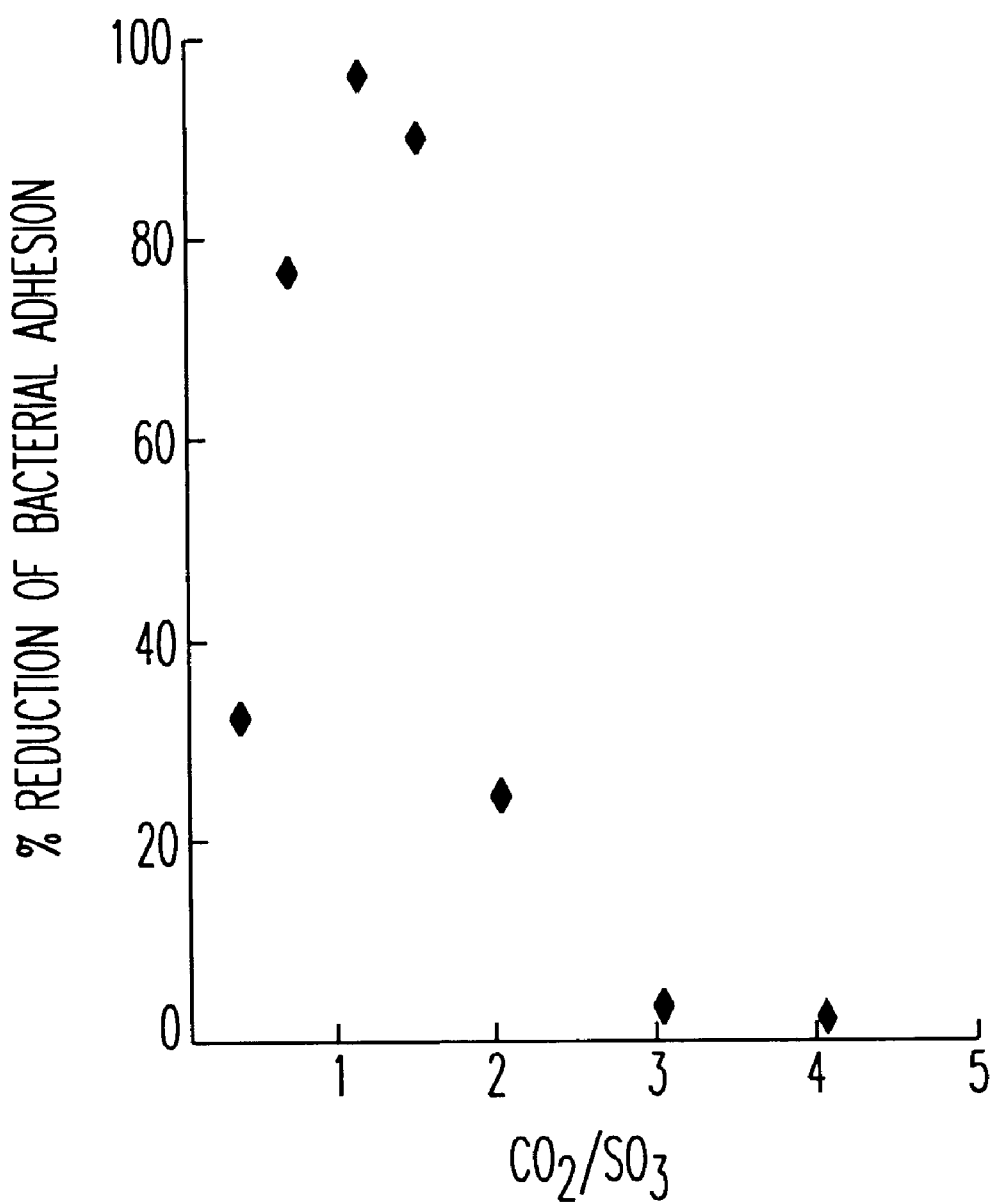

From FIG. 7 it is evident that in the range of the proportion of $CO_2^-/SO_3^-$ up to about 3 there is a marked reduction in the cell growth, whereas around the range between about 2 and about 5 the cell proliferation corresponds approximately to that of the uncoated film and are in any case considerably less reduced than the bacterial adhesion in the same range.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing a bioactive, covalently fixed coating on the surface of a substrate, the process comprising:
preparing a coating polymer which comprises, in copolymerized form,
(i) at least one monomer represented by the formula (I):

$$R-(A)_a \qquad (I),$$

where
R is a mono- or diolefinically unsaturated organic radical having a valence a;
each A is, independently, a carboxylic acid group, sulfuric acid group, sulfonic acid group, phosphoric acid group, phosphonic acid group, phosphorous acid group, a phenolic hydroxyl group, or a salt of one of said acid groups; and
a is 1, 2 or 3; and
(ii) at least one monomer which in copolymerized form is sensitive to ultraviolet radiation; and
then grafting the coating polymer to at least a portion of a surface of a substrate under UV radiative induction, wherein (i) comprises (a) a monomer having carboxylic acid and/or carboxylate groups and (b) a monomer having sulfonic acid and/or sulfonate groups, and the molar proportion of (a)+(b) in the coating polymer is 5 to 40%.

2. The process of claim 1, wherein (i) comprises at least one monomer represented by formula (II) or (III):

$$(C_nH_{2n-q-x})(COOR^1)_x \qquad (II)$$

$$(C_nH_{2n-q-x})(SO_3R^1)_x \qquad (III)$$

wherein each n is, independently, an integer from 2 to 6;
each x is, independently, 1 or 2;
each q is, independently, 0 or 2, and
each $R^1$ is, independently, —H or an equivalent of a metal ion.

3. The process of claim 1, wherein (i) comprises at least one benzene-derived monomer represented by formula IV:

$$(C_6H_m)B_bR^3_c(OH)_d \qquad (IV),$$

wherein m is 6−b−c−d; and each B is, independently, a mono- or diolefinically unsaturated straight-chain or branched radical of the formula $$—(C_nH_k)(COOR^1)_x$$

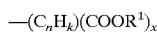

or $$—(C_nH_k)(SO_3R^1)_x,$$

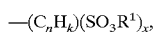

wherein k is 2n−1−g−x;
each n is, independently, an integer from 2 to 6;
each x is, independently, 1 or 2;
each q is, independently, 0 or 2;
each $R^1$ is, independently, —H or an equivalent of a metal ion;
each $R^3$ is, independently, $C_{1-4}$-alkyl, —NH$_2$, —COOH, —SO$_3$H, —OSO$_3$H, —OPO(OH)$_2$, —PO(OH)$_2$, —OP(OH)$_2$, —OPO(O$^-$)OCH$_2$CH$_2$N$^+$(CH$_3$)$_3$, —PO(O$^-$)OCH$_2$CH$_2$N$^+$(CH$_3$)$_3$, —OP(O$^-$)O—CH$_2$CH$_2$N$^+$(CH$_3$)$_3$, or a salt thereof;
b is 1, 2 or 3;
c is 0, 1, 2 or 3; and
d is 0, 1, 2 or 3,
with the proviso that b+c+d is ≦6.

4. The process of claim 1, wherein (i) comprises a monomer having a carboxyl group, a is 2 or 3 or a carboxylate group, and the monomer having a carboxyl group or a carboxylate group includes at least one other radical A which is not a carboxyl group or a carboxylate group; or wherein (i) further comprises a second monomer which has a radical A which is not a carboxyl group or a carboxylate group.

5. The process of claim 1, wherein (a) and (b) are present in a molar ratio, wherein the molar ratio of (a) to (b) is <10.

6. The process of claim 1, wherein (a) and (b) are present in a molar ratio, wherein the molar ratio of (a) to (b) is from 0.5 to 10.

7. The process of claim 1, wherein (a) and (b) are present in a molar ratio, wherein the molar ratio (a) to (b) is from 0.4 to 3, and the coating polymer is antibacterial and inhibits cell proliferation.

8. The process of claim 1, wherein monomer (a) and monomer (b) are present in a molar ratio, wherein the molar ratio of the monomer (a) to the monomer (b) is from 2 to 5, and the coating polymer is antibacterial and promotes cell proliferation.

9. The process of claim 1, wherein the monomer (ii) is a cinnamoyl derivative or furyl derivative.

10. The process of claim 9, wherein (ii) comprises a cinnamoylethyl acrylate or methacrylate.

11. The process of claim 1, wherein the surface of the substrate contains a copolymerized monomer having a group which is sensitive to UV radiation.

12. The process of claim 1, wherein the substrate surface is activated by ultraviolet radiation prior to the grafting step.

13. The process of claim 1, wherein the grafting is induced by ultraviolet radiation.

14. A process according to claim 1, wherein monomer (i) comprises acrylic acid and monomer (ii) comprises cinnamoylethyl methacrylate.

15. A process according to claim 1, wherein the coating polymer is antibacterial and either inhibits or promotes cell proliferation.

16. A process for preparing a covalently fixed coating on the surface of a substrate, comprising:

(a) preparing a coating polymer which comprises, in copolymerized form, (i) at least one monomer represented by the formula (I):

$$R—(A)_a \qquad (I),$$

wherein R is a mono- or diolefinically unsaturated organic radical having a valence a;
each A is, independently, a carboxylic acid group, sulfuric acid group, sulfonic acid group, phosphoric acid group, phosphonic acid group, phosphorous acid group, a phenolic hydroxyl group, or a salt of one of said acid groups; and
a is 1, 2 or 3; and (ii) at least one monomer which is sensitive to ultraviolet radiation; and then (b) dissolving the coating polymer in a solvent;

(c) transferring the coating polymer in the solvent to the surface of the substrate; and (d) grafting the coating polymer to at least a portion of a surface of the substrate under ultraviolet radiative induction.

* * * * *